United States Patent [19]
Fiedler et al.

[11] Patent Number: 5,252,460
[45] Date of Patent: Oct. 12, 1993

[54] IN VITRO DETECTION OF OVA, PARASITES, AND OTHER FORMED ELEMENTS IN STOOL

[76] Inventors: Paul N. Fiedler, 200 Hemlock Rd., New Haven, Conn. 06515; Stephen C. Wardlaw, 191 N. Cove Rd., Old Saybrook, Conn. 06475; Robert A. Levine, 31 Pilgrim La., Guilford, Conn. 06437

[21] Appl. No.: 783,397

[22] Filed: Oct. 28, 1991

[51] Int. Cl.⁵ ................ G01N 33/537; G01N 33/538
[52] U.S. Cl. .................................. 435/7.22; 73/61.43; 73/61.51; 73/61.72; 73/444; 73/149; 422/58; 422/101; 435/7.21; 435/7.23; 435/291; 435/296; 436/63; 436/64; 436/66; 436/165; 436/172; 436/536; 436/541; 436/800; 436/805; 436/810; 436/824
[58] Field of Search .............. 436/536, 541, 63, 64, 436/66, 70, 165, 172, 800, 805, 810, 813, 824; 435/7.22; 422/58, 101; 73/61.43, 61.51, 61.72, 444, 149; 475/7.21, 7.23, 291, 296

[56] References Cited

U.S. PATENT DOCUMENTS

| | | | |
|---|---|---|---|
| 4,027,660 | 6/1977 | Wardlaw et al. | 356/246 |
| 4,077,396 | 3/1978 | Wardlaw et al. | 73/149 |
| 4,082,085 | 4/1978 | Wardlaw et al. | 436/63 |
| 4,085,006 | 4/1978 | Mindick et al. | 435/35 |
| 4,137,755 | 2/1979 | Wardlaw et al. | 73/61.43 |
| 4,159,896 | 7/1979 | Levine et al. | 436/177 |
| 4,190,328 | 2/1980 | Levine et al. | 436/800 |
| 4,567,754 | 2/1986 | Wardlaw et al. | 73/61.43 |
| 4,717,660 | 1/1988 | Schulte | 435/30 |
| 4,774,965 | 10/1988 | Rodriguez et al. | 73/61.43 |
| 4,843,869 | 7/1989 | Levine et al. | 73/61.43 |
| 4,875,364 | 10/1989 | Levine et al. | 436/70 |
| 4,940,668 | 7/1990 | Wardlaw et al. | 436/63 |
| 4,952,054 | 9/1990 | Levine et al. | 73/61.43 |

*Primary Examiner*—David Saunders
*Assistant Examiner*—Christopher L. Chin
*Attorney, Agent, or Firm*—William W. Jones

[57] ABSTRACT

A biologic sample such as feces, sputum, cervical tissue, pleural fluids, exudates, cytologic specimens, or the like, is tested for the presence or absence of: ova; parasites; microorganisms; inflammatory, neoplastic tissue cells; or other target materials which are indicative of infestation, disease or infection. The sample is mixed with a buffer fluid and placed in a transparent tube which contains a volume-constricting cylindrical insert for gravimetric separation of components of the sample. The mixture is centrifuged, and the annular space between the insert and tube bore is examined under magnification for the presence of the target materials.

8 Claims, 1 Drawing Sheet

IN VITRO DETECTION OF OVA, PARASITES, AND OTHER FORMED ELEMENTS IN STOOL

TECHNICAL FIELD

This invention relates to the identification of target materials in biological samples, which materials are indicative of disease, parasite infestation, or the like. More particularly, this invention relates to the detection of ova; parasites, either free living or in cysts; microorganisms; neoplastic or inflammatory tissue cells, all in biological samples, such as feces, pleural fluids, exudates, cytologic specimens, or the like.

BACKGROUND ART

Biological samples are routinely examined for the presence of abnormal organisms or cells, such as ova, parasites, microorganisms, and inflammatory cells by conventional light microscopy of smear preparations. Visual detection of such materials in smears is hindered by the presence of masking particulate or other matter interspersed between cells. Additionally, standard smear preparations utilize only a minute fraction of the sample since the smears must be thin enough to allow the passage of light. Examination of multiple smears to compensate for these drawbacks is impractical in the busy hospital laboratory. Consequently, the sensitivity of disease detection is suboptimal using the smear methodology.

Ova and parasites present in stool may be concentrated by employing filtration techniques whereby the sample specimen is made relatively dense so that the ova, and/or parasites, and/or cysts will float on the surface of the sample. This technique however does not permit the visualization of the target organisms or ova in the concentrated specimen. The target layer must be aspirated or transferred to a slide for examination, whereupon a large number of the target organisms or cysts are lost.

Cytologic evaluation of tissue cells in smears derived from biological fluids and tissues for the purpose of diagnosing cancer is an integral part of the practice of medicine. These examinations are; however, typically performed on less than 5% of the cells sampled due to the aforesaid requirement that smears be thin. Furthermore, as noted, tissue cells in these preparations are often obscured from view by contaminating blood cells and debris.

Cytologic evaluation of tissue cells in feces for the diagnosis of colon cancer has not been used to any significant extent. In fact, the index of a recently published authoritative cytology textbook (*Comprehensive Cytopathology*, Marluce Bibbo; ed. W. B. Saunders Company, 1991) contains no references to either stool or feces evaluation. This deficit may be explained by the paucity of tissue cells in the standard stool smear, and the abundance of obscuring debris. Consequently, cytologic examination of stool by the smear protocol is virtually useless as part of a cancer screening.

Medical diagnostics of stool and other biological samples would be greatly improved by a technique which does not depend on the use of a very limited amount of sample material, such as is inherent in the examination of specimen smears. The reason for this is that when one is able to use a larger specimen sample in the screening or examination, the odds are increased that target materials will be included in the sample and identified.

U.S. Pat. No. 4,190,328 granted Feb. 26, 1980 to R. A. Levine et al describes a process for the detection of blood-borne parasites in a sample of centrifuged anticoagulated whole blood. The blood sample is mixed with a stain and then centrifuged in a tube containing a volume-restricting float. Target parasites which may be in the blood sample are highlighted by the stain and trapped between the float and the bore of the tube where they can be visually observed under appropriate magnification.

U.S. Pat. No. 4,717,660 granted Jan. 5, 1988 to T. H. Schulte discloses a procedure for detecting bacteria in an anticoagulated blood sample, and for assessing phagocytic activity in the blood sample. The blood sample is mixed with a stain that will highlight the bacteria, and the mixture is centrifuged in a tube containing a volume-restricting float. The buffy coat in the centrifuged blood sample settles into the restricted space between the tube bore and float, and the cell bands in the buffy coat are thereby physically elongated. Any bacteria in the blood will be differentially stained and will be located in one of the buffy coat cell bands, where such bacteria can be observed under appropriate magnification.

The aforesaid patented procedures are restricted to diagnosing blood samples, and do not suggest any diagnostic procedures wherein non-fluid biological samples, or fluid biological samples, other than blood, can be analyzed quickly and dependably for target malady-specific materials.

DISCLOSURE OF THE INVENTION

This invention relates to the detection of target malady-specific materials in fluid and non-fluid biological specimen samples. Target materials detectable by this invention include: parasites; parasite ova; parasite cysts; microorganisms; neoplastic or inflammatory tissue cell; and the like. Specimen samples which can be examined using this invention include: feces; cytological specimens; pleural fluids; exudates; and the like.

The examination of the specimen is made in a transparent tube which contains an insert operable to limit the available volume in the tube into which the target materials will settle upon centrifugation of the sample in the tube. The tube can be a capillary tube, or, if necessary, it can be larger in volume for examining certain biological specimens, such as feces. The insert in the tube is generally cylindrical and is made from a plastic material having a specific gravity which ensures that the target materials, if present, will settle into the annular free space between the insert and the tube bore wall. In most cases, a specific gravity which ensures that the insert will sink during centrifugation to the bottom of the specimen sample tube will suffice for proper performance of the invention; however, in some cases it may be desirable to have the insert "float on" or "settle into" one of the centrifuged component layers. Stains or other colorants may be incorporated into the tube in a dry coating on the tube bore, to be released when the specimen is added to the tube. When non-liquid or non-fluid specimens are being examined, or when minute amounts of a fluid specimen are being examined, a liquid medium will be added to the specimen tube in order to provide an environment in the tube in which the target materials, if present, will be separated and isolated from the rest of the specimen. When larger preevacuated centrifuge tubes and inserts are used, as described in copending U.S. patent application Ser. No. 579,274, filed Sep. 5, 1990 by Levine and Wardlaw, all necessary liquid reagents or buffers may be preloaded in the tube.

This method for the detection of ova, cysts, parasites, or other microorganisms, inflammatory and tissue cells in stool and other biological samples is far more sensitive than conventional smears. The increased sensitivity derives from the ability to analyze a large sample volume (1 ml) of a sample suspension rapidly and accurately. More than one thousand conventional smears corresponding to approximately six hundred man-hours would be required for light microscopy examination of a 1 ml sample volume.

This invention utilizes centrifugation to concentrate the particulate matter in feces and other biologic samples at the bottom or the top of a glass tube. The target ova, parasites, other microorganisms, tissue cells, or the like in the sample form a separate discrete layer. Targets in the layer are pressed against the side of the tube by the plastic insert which has the same specific gravity as the targets. The insert is of appropriate dimensions to spread these target elements in a thin film along the sides of the tube thereby bringing the targets into the focal plane of a fluorescent microscope. Acridine orange present in the tube stains the DNA of cells green and the RNA red. The metachromatic fluorescent staining allows the identification of the targets, and, in the case of assay for cancer cells, enables the classification of epithelial and other tissue cells as benign or malignant. The juxtaposition of cells of the same class facilitates the comparison of nuclear and cytoplasmic features between cells, a process which is essential to the diagnosis of malignancy.

It is therefore an object of the invention to provide an improved technique for assaying a biological specimen sample for target malady-specific materials.

It is a further object of the invention to provide a technique of the character described wherein a relatively large volume of the biological sample can be assayed quickly and easily, while providing accurate data.

It is yet another object of the invention to provide a technique of the character described wherein the biological sample being assayed can be a non-fluid material, such as feces.

It is an additional object to provide a technique of the character described wherein the presence of cancer cells in the biological sample can be detected.

These and other objects and advantages of the invention will become more readily apparent from the following detailed description of several preferred embodiments of this invention when taken in conjunction with the accompanying drawings in which:

DETAILED DESCRIPTION OF THE BEST MODE

Figure 1:
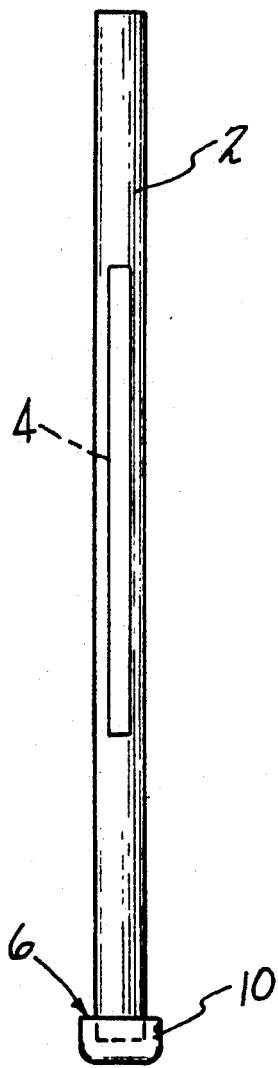
FIG. 1 is side elevational view of a centrifuge tube assembly for use in performing the procedure of this invention.
Figure 2:
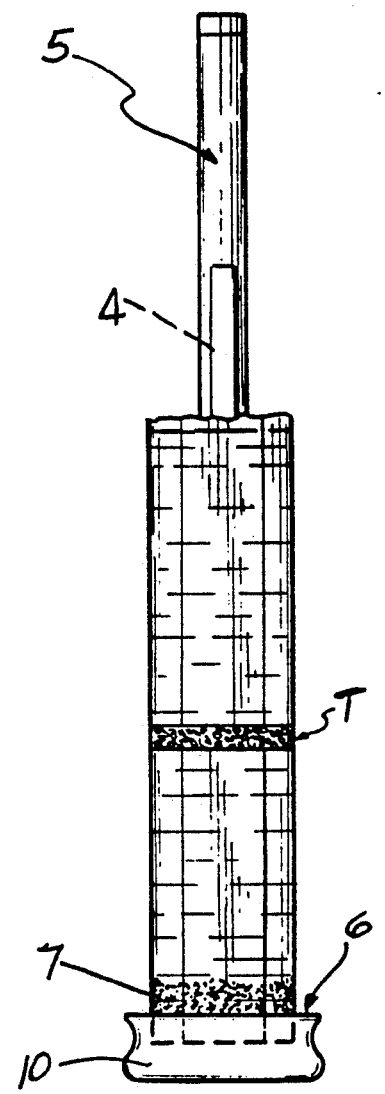
FIG. 2 is a view of the tube assembly of FIG. 1 showing a centrifuged specimen sample therein, and with the target-containing area in the tube assembly being blown up in size to point out the nature of the invention.

Referring now to FIGS. 1 and 2, there is shown in FIG. 1, a tube 2, which may be a glass capillary tube, or other transparent tube, and which contains an insert 4 made of a plastic, which has a specific gravity that causes the insert 4 to settle through the biological sample mixture 5 to the bottom 6 of the tube 2, when the latter is centrifuged with the biological sample therein. Any fibrous or other solid components in the sample may settle into a clump 7 in the bottom of the tube 2 and the targets form a band T in the annulus between the insert 4 and tube 2. A plastic cap 10 closes the bottom 6 of the tube 2 prior to centrifugation. In certain cases, as when feces is being examined, the insert 4 may imbed itself in the clump 7.

The following describes a general procedure for preparing biological samples for analysis in accordance with this invention, and a number of specific examples of sample analyses are also set forth.

In each of the examples described hereinafter, the biological sample was mixed with a buffer solution consisting of Dulbecco's phosphate buffered saline with 0.15% EDTA. The bottom of the tube was plugged with 4% agarose (1 cm) and a plastic cap. Samples were spun in the tube, along with an acridine orange stain and the plastic insert, for five minutes at 12,000 rpm prior to visual inspection by fluorescent microscopy at 500× power. The tubes used in the following examples were microhematocrit or capillary tubes, however, larger tubes and inserts can be used when larger samples need to be inspected. Other buffer solutions and dyes or stains can be used depending on the nature of the samples being assayed.

EXAMPLE 1

One gm of fresh solid stool, which was intentionally altered by the addition thereto of parasites to simulate infestation, was placed in 3 ml of buffer. The mixture was vortexed until homogeneous, and the centrifuge tube was filled with an aliquot of the homogeneous mixture. After centrifugation, particulate material was seen to layer out at the bottom of the tube and the plastic insert was embedded in the particulate matter layer. Lighter constituents were trapped between the insert and tube bore. These lighter trapped constituents were examined under a fluorescent microscope, and were found to include ova, parasites, granulocytes, epithelial cells, bacterial and yeast. The aforesaid examination revealed that the procedure can detect in stool both parasite infestation and other cell types that may be indicative of disease or infection.

EXAMPLE 2

One ml of ascites fluid obtained by paracentesis was centrifuged to form a loose pellet. Ten ul of the formed pellet was placed in 1 ml of the buffer to which mixture 20 ul of whole blood (EDTA), to duplicate a naturally bloody sample, and to which buccal epithelial scrapings were added in order to increase potential target cells, whereby the applicability of the invention to performing cervical PAP tests could be confirmed. The resultant mixture was vortexed briefly to blend the constituents homogeneously, and the centrifuge tube with insert was then filled with a portion of the resultant mixture. After centrifugation, the plastic insert extended from the bottom of the tube through all cell layers. Upon microscopic examination, it was determined that the nontarget formed debris consisting of erythrocytes, followed by granulocytes, monocytes, and lymphocytes were layered out at the bottom. The top layer was a mixture of target epithelial cells, mesothelial cells and platelets. Excellent separation of blood and non-blood cells was achieved, as is necessary in cytological analysis. The concentration of cells between the insert and tube wall enabled easy differentiation of normal and abnormal cells.

EXAMPLE 3

Cells obtained by swabbing the endo and ectocervical mucosae of a fresh cone biopsy specimen were placed in 1 ml of the buffer, to which 1 ml of a mucolytic agent (0.1 gm N-acetyl cysteine in 10 ml sodium citrate diluted 3:4 with water to 300 m OSM) was added. The mixture was vortexed briefly to form a homogeneous sample, and a capillary tube was filled with a portion of the mixed sample. The filled tube was then centrifuged and examined. The insert extended through all cell layers in the sample. Fluorescent microscopy revealed highly dysplastic squamous cells and atypical endocervical cells in the area between the insert and tube. Cancer cells can thus be readily observed in the sample using the procedure of this invention. Additionally, more subtle cell changes can be identified using the invention. For example, atypical stage cells, i.e., cells which are in the process of transforming from a normal to a cancerous morphology, are readily identified using the procedure of this invention.

Various target-highlighting reagents such as acridine orange stain; antibodies coupled with fluorophore; or polyvalent target-agglutinating antibodies can be included in the tube in order to render the targets more readily observable. The agglutinating antibodies can be used to bind targets together whereby they will be observed in a better defined band in the annulus.

Since many changes and variations of the disclosed embodiments of the invention may be made without departing from the inventive concept, it is not intended to limit the invention otherwise than as required by the appended claims.

What is claimed is:

1. A method for in vitro testing of patients' stool samples for the presence or absence of parasites or their ova or cysts which are indicative of parasite infestation in the patient, said method comprising the steps of:
    a) providing a transparent sample-receiving tube containing a volume-restricting generally cylindrical insert positioned substantially coaxially with the tube axis, said insert being operable to produce a restricted volume annulus in the tube adjacent the tube side wall and a highlighting reagent for visually differentiating the parasites, ova, or cysts from remaining constituents of the sample;
    b) forming a homogeneous mixture of the stool sample and a liquid dispersant;
    c) substantially filling said tube with said mixture;
    d) centrifuging said filled tube to gravimetrically separate any parasites, ova or cysts from other formed components in the mixture; and
    e) examining said annulus under magnification to determine the presence or absence of parasites, ova or cysts in said annulus.

2. The method of claim 1 wherein said reagent is acridine orange.

3. The method of claim 1 wherein said reagent comprises antibodies specific for said parasites or their ova or cysts coupled with fluorophore.

4. The method of claim 1 wherein said reagent comprises agglutinating antibodies that are specific for said parasites or their ova or cysts.

5. A method for in vitro testing of patients' stool samples for the presence or absence of neoplastic or inflammatory tissue cells which are indicative of disease or infection in the patient, said method comprising the steps of:
    a) providing a transparent sample-receiving tube containing a volume-restricting generally cylindrical insert positioned substantially coaxially with the tube axis, said insert being operable to produce a restricted volume annulus in the tube adjacent the tube side wall and a cell highlighting reagent for visually differentiating said cells from remaining constituents of the sample;
    b) forming a homogeneous mixture of the stool sample and a liquid dispersant;
    c) substantially filling said tube with said mixture;
    d) centrifuging said filled tube to gravimetrically separate any of said cells from other formed components in the mixture; and
    e) examining said annulus under magnification to determine the presence or absence of said cells in said annulus.

6. The method of claim 5 wherein said reagent is acridine orange.

7. The method of claim 5 wherein said reagent comprises antibodies specific for said neoplastic or inflammatory tissue cells coupled with fluorophore.

8. The method of claim 5 wherein said reagent comprises agglutinating antibodies that are specific for said neoplastic or inflammatory tissue cells.

* * * * *